United States Patent
Tsai et al.

(10) Patent No.: US 6,262,299 B1
(45) Date of Patent: Jul. 17, 2001

(54) ZWITTERIONIC MONOMER HAVING AMINO-MULTICARBOXYLIC ACID FUNCTIONALITY

(75) Inventors: John Tsai, Belle Mead, NJ (US); Sirisoma Wanigatunga, Largo, FL (US)

(73) Assignee: National Starch and Chemical Investment Holding Corporation, Wilmington, DE (US)

( * ) Notice: Subject to any disclaimer, the term of this patent is extended or adjusted under 35 U.S.C. 154(b) by 0 days.

(21) Appl. No.: 09/348,085

(22) Filed: Jul. 6, 1999

(51) Int. Cl.$^7$ .................................................. C07C 69/63
(52) U.S. Cl. ..................... 560/222; 260/482; 260/459; 536/60
(58) Field of Search .................... 560/222; 260/482, 260/459

(56) References Cited

U.S. PATENT DOCUMENTS

| | | | |
|---|---|---|---|
| 2,777,872 | * | 1/1957 | Drake et al. . |
| 2,935,493 | | 5/1960 | Schuller et al. ................. 260/72 |
| 2,958,682 | | 11/1960 | Schuller et al. ................. 260/80.3 |
| 3,473,998 | | 10/1969 | Spriestersbach et al. .......... 161/177 |
| 3,478,001 | | 11/1969 | Dormagen et al. .............. 260/79.3 |
| 3,497,482 | | 2/1970 | Hwa et al. .................... 260/79.3 |
| 3,671,502 | * | 6/1972 | Samour et al. . |
| 4,009,201 | * | 2/1977 | Steckler et al. . |
| 5,500,087 | * | 3/1996 | Bernard et al. . |

FOREIGN PATENT DOCUMENTS

0689829 * 3/1996 (EP) .

* cited by examiner

Primary Examiner—Paul J. Killos
Assistant Examiner—Fred Zitomer
(74) Attorney, Agent, or Firm—Thomas F. Roland

(57) ABSTRACT

A zwitterionic monomer having amino-multicarboxylic acid functionality having Structure (I)

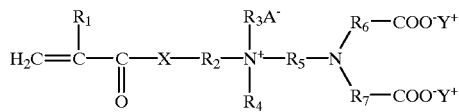

wherein $R_1$ is selected from the group consisting of H, an alkyl group having 1 to 6 carbon atoms; $R_2$ is $(CH_2)_n$ where n is 2 to 12; $R_3$ and $R_4$ are independently an alkyl group having 1 to 6 carbon atoms; $R_5$ is $(CH_2)_m$ where m is 2 or 3; $R_6$ and $R_7$ are independently selected from

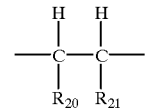

wherein $R_{20}$ is selected from the group consisting of H, $CH_3$, and COOY; $R_{21}$ is selected from H or $CH_3$; X is oxygen or nitrogen; A is a halide; and Y is independently a cation. The zwitterionic monomer is the reaction product of an amino-multicarboxylic acid and an amine containing monomer. Polymers prepared with the zwitterionic monomer are especially useful in hair treatment compositions to provide increased stiffness to hair, in coating formulations to increase the impact resistance, wet adhesion, and flexibility of the coating, especially wood coatings, and in mortar compositions to improve mortar compatibility, especially with redispersible powders.

6 Claims, No Drawings

ZWITTERIONIC MONOMER HAVING AMINO-MULTICARBOXYLIC ACID FUNCTIONALITY

FIELD OF THE INVENTION

This invention relates to a zwitterionic monomer having amino multicarboxylic acid functionality which is the reaction product of an amino-multicarboxylic acid and an amine containing monomer.

BACKGROUND OF THE INVENTION

Various carboxybetaines, sulfobetaines, homopolymers and copolymers thereof have been described in the prior art. U.S. Pat. Nos. 3,473,998 and 3,478,001 describe sulfobetaines and copolymers thereof with acrylonitrile. U.S. Pat. No. 3,497,482 describes homopolymers of sulfobetaines and copolymers with certain ethylenically unsaturated monomers. U.S. Pat. Nos. 2,777,872; 2,935,493; and 2,958,682 describe carboxybetaines and copolymers thereof with various ethylenically unsaturated compounds. U.S. Pat. No. 3,671,502 describes copolymers comprising units derived from carboxybetaines or sulfobetaines and units derived from hydroxyalkyl acrylates/methacrylates, polyalkylene glycol acrylateslmethacrylates or polyglycerol acrylates/methacrylates. U.S. Pat. No. 5,500,087 describes amino-multicarboxylate starch ether derivatives which are useful as retention and strength aids in papermaking.

However, the prior art does not describe multicarboxybetaine monomers or zwitterionic monomers having amino-multicarboxylic acid functionality. Moreover, the prior art does not describe preparing copolymers from such monomers.

SUMMARY OF THE INVENTION

The present invention provides a zwitterionic monomer having, amino-multicarboxylic acid functionality having Structure (I)

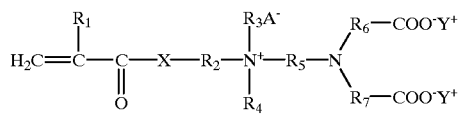

wherein $R_1$ is selected from the group consisting of H, an alkyl group having 1 to 6 carbon atoms; $R_2$ is $(CH_2)_n$ where n is 2 to 12; $R_3$ and $R_4$ are independently an alkyl group having 1 to 6 carbon atoms; $R_5$ is $(CH_2)_m$ where m is 2 or 3; $R_6$ and $R_7$ are independently selected from

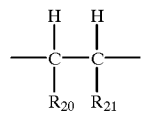

wherein $R_{20}$ is selected from the group consisting of H, $CH_3$, and COOY; $R_{21}$ is selected from H or $CH_3$; X is oxygen or nitrogen; A is a halide; and Y is independently a cation;

said zwitterionic monomer is the reaction product of an amino-multicarboxylic acid and ar amine containing monomer, wherein the amino-multicarboxylic acid has Structure (II)

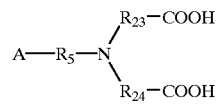

and the amine conitaining monomer has Structure (III)

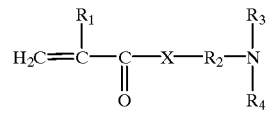

wherein $R_{23}$ and $R_{24}$ are independently selected from

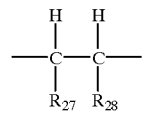

wherein $R_{27}$ is selected from the group consisting of H, $CH_3$, and COOH; and $R_{28}$ is H or $CH_3$.

The zwitterionic monomers of the invention have at least two carboxyl groups which are in close vicinity to each other in the monomer. The zwitterionic monomers may be polymerized alone or in combination with at least one other monomer to form a polymer having unique properties. Polymers prepared with the zwitterionic monomer are especially useful in hair treatment compositions to provide increased stiffness to hair, in coating formulations to increase the impact resistance, wet adhesion, and flexibility of the coating, especially wood coatings, and in mortar compositions to improve mortar compatibility, especially with redispersible powders.

DESCRIPTION OF THE INVENTION

The zwitterionic monomer having amino-multicarboxylic acid functionality is prepared by reacting an amino-multicarboxylic acid with an amine containing monomer. The zwitterionic monomer having amino-multicarboxylic acid functionality having Structure (I)

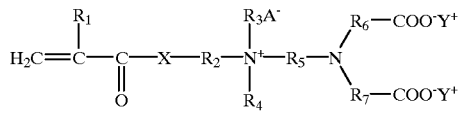

wherein $R_1$ is selected from the group consisting of H, an alkyl group having 1 to 6 carbon atoms; $R_2$ is $(CH_2)_n$ where n is 2 to 12; $R_3$ and $R_4$ are independently an alkyl group having 1 to 6 carbon atoms; $R_5$ is $(CH_2)_m$ where m is 2 or 3; $R_6$ and $R_7$ are independently selected from

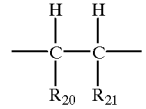

wherein $R_{20}$ is selected from the group consisting of H, $CH_3$, and COOY; $R_{21}$ is selected from H or $CH_3$; A is a halide, preferably chloride or bromide; and Y is independently a cation, preferably H, alkali metal, alkaline earth metal, or ammonium.

The amino-multicarboxylic acid has Structure (II)

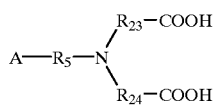

wherein $R_5$ is $(CH_2)_m$ where m is 2 or 3; $R_{23}$ and $R_{24}$ are independently selected from

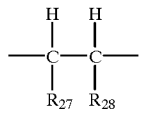

wherein $R_{27}$ is selected from the group consisting of H, $CH_3$, and COOH; $R_{28}$ is H or $CH_3$, A is a halide, preferably chloride or bromide.

The amino-multicarboxylic acid is preferably prepared by a Michael reaction between an amine of an aminoalcohol, preferably a primary amine, and an olefin containing ester followed by halogenation with any halide and preferably chlorination or bromination. More preferably chlorination is used. The chlorination may be carried out using chloride compounds such as thionyl chloride or phosphorus oxychloride. Purification such as by steam stripping or recrystallization from isopropanol or other suitable solvents may be employed.

The amino alcohol used in preparing the amino-multicarboxylic acid has structure (IV):

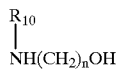

wherein $R_{10}$ is H or an alkyl group having 1 to 18 carbon atoms, preferably 1 to 8 carbon atoms, m is 2 or 3.

The olefin containing ester has Structure (V):

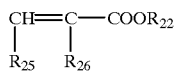

wherein $R_{25}$ is selected from H, $CH_3$, or $COOR_{22}$; $R_{26}$ is selected from H or $CH_3$; and $R_{22}$ is an alkyl group having 1 to 6 carbon atoms, preferably 1 to 3 carbon atoms. Preferably, the olefin containing ester is selected from alkyl acrylates, alkyl methacrylates, alkyl crotonates, dialkyl maleate, or dialkyl fumarate.

In one embodiment of the invention where $R_{10}$ is hydrogen then any olefin containing ester is acceptable for the reaction. If $R_{10}$ is an alkyl group then the olefin containing ester must be a diester. Preferred diesters are dialkyl maleate and dialkyl fumarate, wherein the alkyl group has 1 to 6 carbon atoms.

In one embodiment of the invention, the amino-multicarboxylic acid is prepared by reacting ethanolamine with methyl acrylate followed by chlorination with thionyl chloride and hydrolysis to provide the aminodicarboxyl containing reagent, 2-chloroethylaminodipropionic acid. A preferred reaction scheme is as follows:

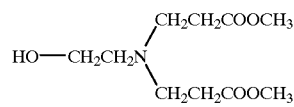
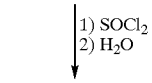
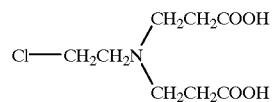

An amine containing monomer is reacted with the amino-multicarboxylic acid to form the zwitterionic monomer having amino-multicarboxylic acid functionality. The amine containing monomer has Structure (III):

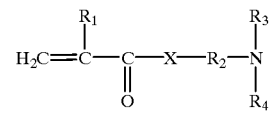

wherein $R_1$ is selected from the group consisting of H, an alkyl group having 1 to 6 carbon atoms; $R_2$ is $(CH_2)_n$ where n is 2 to 12; $R_3$ and $R_4$ are independently an alkyl group having 1 to 6 carbon atoms; and X is oxygen or nitrogen.

The formation of the zwitterionic monomer having amino-multicarboxylic acid functionality involves reacting the amine containing monomer with the amino-multicarboxylic acid in an aqueous medium at a temperature of from about 10° C. to 95° C., preferably from about 20° C. to 50° C. The reaction is carried out under alkaline conditions at a pH of from about 8.5 to 13, more particularly from about 9.5 to 12.5. The pH is conveniently controlled by the periodic addition of a dilute aqueous solution of sodium hydroxide or other common base including potassium hydroxide, calcium hydroxide, sodium carbonate, ammonium hydroxide, tetramethylammonium hydroxide, etc. The preferred bases are sodium and potassium hydroxide.

The amino-multicarboxylic acid may be added to the reaction mixture as a solid or an aqueous solution. The preferred concentration of the solution is 20 to 50% by weight, based on the weight of the reagent. In an alternative method, the amino-multicarboxylic acid solution is brought to the desired alkaline pH prior to its addition to the amine containing monomer. In this alternative method, the reagent is in the form of a salt rather than an acid or partially neutralized acid when it is introduced to the reaction mixture.

Reaction time will vary from about 0.2 to 24 hours depending on such factors as the stability and reactivity of the amino-multicarboxylic acid employed, the temperature, pH, the scale of the reaction. In general, the preferred range of reaction time is from about 1 to 16 hours.

After completion of the reaction, the pH of the reaction mixture is adjusted to from about 3 to 9 with any commercial acid such as hydrochloric acid, sulfuric acid, acetic acid, etc. Such acids may be conventionally added as a dilute aqueous solution. Depending on the final pH and the base used, the carboxyl group can be present as either the carboxylic acid or the corresponding salt.

Recovery of the zwitterionic monomer having amino-multicarboxylic acid functionality may be readily accomplished by methods known in the art such as precipitation.

5

The following nonlimiting examples illustrate further aspects of the invention.

EXAMPLE 1

Preparation of an Amino-multicarboxylic Acid Reagent (2-chloroethylaminodipropionic acid).

A 1L three neck round bottom flask fitted with a water cooled condenser, mechanical stirrer and addition funnel was charged with 30 g (0.49 mole) of ethanolamine. The flask was cooled to 10° C. and 84.6 g (0.98 mole) of methyl acrylate was charged to the addition funnel. One half of the methyl acrylate was added slowly to the reaction at such a rate as to maintain the reaction temperature at or below 10° C. Ethyl acetate was added to help solubilize the forming solid.

The second half of the methyl acrylate was added slowly to the reaction while keeping the temperature at or below 10° C. When the addition was completed, the reaction was slowly warmed to room temperature and then heated to 48° C. and held for 18 hours to form an intermediate (hydroxyethylaminodipropionate methyl ester).

The hydroxyethylaminodipropionate methyl ester was chlorinated according to the following procedure: An addition funnel was charged with 183.4 ml (2.50 mole) of thionyl chloride ($SOCl_2$) and added to the hydroxyethylaminodipropionate methyl ester with cooling, maintaining the temperature below 20° C. After the addition was completed, the reaction was heated to 80° C. to 90° C. and held for 2 hours. The reactor was cooled to less than 30° C., and approximately 75 ml of water was added to destroy any residual thionyl chloride and liberate the free acid. The water and other volatiles were removed under vacuum and the product was purified by precipitation into isopropanol. The structures of the 2-chloroethylaminodipropionic acid and hydroxyethylaminodipropionate methyl ester were confirmed by NMR. Chlorine analysis of the 2-chloroethylaminodipropionic acid was determined to be 13.57 percent organic chlorine (98.7 percent of theoretical).

EXAMPLE 2

Preparation of an Amino-multicarboxylic Acid Reagent (2chloroethylaminodipropionic acid).

The procedure according to Example 1 was used except that methyl acrylate was replaced with ethyl acrylate. The structures of the 2-chloroethylaminodipropionic acid and hydroxyethylaminodipropionate ethyl ester were confirmed by NMR. Chlorine analysis of the 2-chloroethylaminodipropionic acid was determined to be 13.61 (99% of theoretical) percent organic chlorine.

EXAMPLE 3

Preparation of Zwitterionic Monomer Containing an Amino-multicarboxylic Functionality dimethylaminopropylmethacrylate, 2-choroethylaminodipropionic acid (DMAPMA/CEPA).

A 25% solution of the 2-chloroethylaminodipropionic acid prepared in Example 1, 130 g, and 98.6 g of a 20.27% solution of NaOH (0.125 mole) was slowly added to a beaker containing 21.25 g of dimethylaminopropylmethacrylamide (DMAPMA) while maintaining a pH of 9.2 to 9.4 and a temperature of 10° C. to 15° C. using an ice water bath. After the addition of the NaOH was complete, the temperature of the reaction mixture was raised to 40° C. and maintained with stirring for three hours. The reaction product was cooled to approximately 25° C. and stirring was continued for 16 hours. The product appeared light yellow in color. NMR spectral analysis indicated 100% of the monomer was synthesized.

EXAMPLE 4

Preparation of Zwitterionic Monomer Containing an Amino-multicarboxylic Functionality.

A 50% solution of the 2-chloroethylaminodipropionic acid prepared in Example 1, 130 g, and 80 g of a 50% solution of NaOH was slowly added to a beaker containing 85.0 g of a 50% aqueous solution of dimethylaminopropylmethacrylamide (DMAPMA) while maintaining a pH of about 9.0 and a temperature of 10° C. to 15° C. using an ice water bath. After the addition of the NaOH was complete, the temperature of the reaction mixture was raised to 40° C. and maintained with stirring for three hours. The reaction product was cooled to about 25° C. and appeared brownish yellow in color. The product had a pH of 9. NMR spectral analysis indicated 75% of the monomer was synthesized.

EXAMPLE 5

Preparation of Zwitterionic Monomer Containing an Amino-multicarboxylic Functionality.

A 50% solution of the 2-chloroethylaminodipropionic acid prepared in Example 1, 130 g, and 74 g of a 50% solution of NaOH was slowly added to a beaker containing 85.0 g of a 50% aqueous solution of dimethylaminopropylmethacrylamide (DMAPMA) while maintaining a pH of about 8.0 and a temperature of 10° C. to 15° C. using an ice water bath. After the addition of the NaOH was complete, the temperature of the reaction mixture was raised to 40° C. and maintained with stirring for six hours. The reaction product was cooled to about 25° C. and appeared brownish yellow in color. The product had a pH of 8. NMR spectral analysis indicated 100% of the monomer was synthesized, as indicated by the disappearance of DMAPMA tertiary amine peak at 45 ppm, and the appearance of peak at 50 ppm due to quarternary ammonium peak. Some polymerization reaction was also observed.

EXAMPLE 6

Preparation of an Aminomulti-carboxylate Acid Reagent, i.e., 2-chloroethyl, N-methylaminosuccinic Acid.

A 250 ml 3-neck round bottom flask fitted with a water cooled condenser, mechanical stirrer and addition funnel was charged with 60 g (0.80 mole) of N-methylaminoethanol. Dimethyl maleate (115.3 g, 0.80 mole) was added slowly over about 30 minutes with agitation. The reaction was warmed to 45° C. and stirred for 18 hours. When the reaction was complete, the product was transferred with 75 ml of toluene to a 1,000 ml 4-neck round bottom flask equipped with addition funnel, mechanical stirrer, oil bath and distillation head. The addition funnel was charge with 110 ml of thionyl chloride and added to the reaction slowly to keep the temperature at or below 35° C.. After addition, the reaction was heated to 80° C. for 30 minutes. The toluene was steam distilled until the head temperature reached 98 to 100° C. for three minutes. The product was cooled and filtered and then analyzed and gave acceptable chlorine and NMR values, indicating the desired compound, i.e., 2-chloroethyl, N-methylaminosuccinic acid, had been prepared.

This reagent was reacted with DMAPMA in a similar procedure to the Example 3 to produce a zwitterionic monomer having amino-multicarboxylic acid functionality.

EXAMPLE 7

Preparation of Copolymer of Butyl Acrylate/Methyl Methacrylate/Methacrylic Acid/DMAPMA/CEPA Prepared in Example 3 in a Corresponding Ratio of (38:29:13:20)

A mixture of 38 g of butyl acrylate, 29 g of methyl methacrylate, 13 g of methacrylic acid, and 22 g of ethanol, was prepared. Thirty percent of the mixture was heated to reflux with 0.74 g (dissolved in 11 g of ethyl alcohol) of tert butyl peroctoate initiator. After 5 minutes, the remaining seventy percent of the mixture was added dropwise by means of an addition funnel to the reactor over three hours. Simultaneously, in a separate addition funnel, 40 g of a 50% aqueous solution of the zwitterionic monomer prepared in Example 3 was added dropwise to the reactor over three hours. Two hours after starting the monomer slow adds, 25 g of 1.5% solution of initiator solution in ethanol was added over a period of two hours. The contents were held at reflux for another 4.5 hours. The contents were cooled.

Into 220 g of polymer solution at reflux, 12.1 g of 3-aminopropanol in 100 g of water was added to neutralize the carboxylate functionality of the copolymer. The contents were steam stripped to remove ethanol. The resulting copolymer emulsion was cooled, filtered, and diluted to 15% solids.

EXAMPLE 8 (Comparison)
Preparation of a Copolymer of Butyl acrylate/Methyl methacrylate/Methacrylic acid/N,N-dimethyl-N-methacryloxyethyl-N-(3-sulfopropylammonium Betaine Inner Salt (SPE).

The polymerization procedure according to Example 7 was used except that N,N-dimethyl-N-methacryloxyethyl-N-(sulfopropyl)ammonium betaine inner salt (SPE) replaced the zwitterionic monomer of the invention.

EXAMPLE 9 (Comparison)
BALANCE which is available from National Starch and Chemical Company is prepared from Butyl Acrylate/Methyl Methacrylate/Methacrylic Acid in the corresponding ratio of (44:43:13) according to a similar procedure as set forth in Example 7.

EXAMPLE 10
Comparison of Copolymers in Hair Spray Applications.

The zwitterionic polymer having aminodicarboxylic acid functionality prepared in Example 7 was evaluated in a 55% VOC hair spray application. The copolymer BALANCE, available from National Starch and Chemical Company, was also evaluated in a 55% VOC hair spray application. Eight evaluators compared hair tresses which were independently treated with each of the hair sprays, and made a determination as to which hair tress exhibited more desirable performance properties. The test results are summarized in Table I.

TABLE I

| Polymer | Gloss | Stiffness | Dry Comb | Flake |
|---|---|---|---|---|
| Example 7 (Copolymer of invention) | 7/8 | 8/8 | 4/8 | 4/8 |
| Example 9 (BALANCE) | | | | |

The results in Table I show that seven out of the eight evaluators preferred the zwitterionic copolymer of Example 7 as compared to the commercially available copolymer BALANCE for gloss. Table I further shows that eight out of eight evaluators preferred the zwitterionic copolymer of Example 7 as compared to the commercially available copolymer BALANCE for stiffness properties. The evaluators determined that the dry-comb property and flake property were equal between the tresses. Thus, the results in Table I clearly show the superior stiffness properties of the copolymers of the invention as compared to commercially available copolymers.

EXAMPLE 11
Comparison of Copolymers in Hair Spray Applications.

The zwitterionic polymer having aminodicarboxylic acid functionality prepared in Example 7 was evaluated in a 55% VOC hair spray application. In addition, the copolymer prepared in Example 8 containing SPE was evaluated in a 55% hair spray application. Eight evaluators compared hair tresses which were independently treated with each of the hair sprays, and made a determination as to which hair tress exhibited more desirable performance properties. The test results are summarized in Table II.

TABLE II

| Polymer | Gloss | Stiffness | Dry Comb | Flake |
|---|---|---|---|---|
| Example 7 (Copolymer of invention) | 5/8 | 7/8 | 4/8 | 4/8 |
| Example 8 (Copolymer with SPE) | | | | |

The results in Table II show that five out of the eight evaluators preferred the zwitterionic copolymer of Example 7 as compared to the copolymer of Example 8 for gloss. Table II further shows that seven out of eight evaluators preferred the zwitterionic copolymer of Example 7 as compared to the copolymer of Example 8 for stiffness properties. The evaluators determined that the dry-comb property and flake property were equal between the tresses. Thus, the results in Table II clearly show the superior stiffness properties of the copolymers of the invention.

EXAMPLE 12

A polyurethane dispersant was prepared by reacting polypropylene glycol, isophorone diisocyanates, and dihydroxymethyl propionic acid.

An emulsion polymerization containing butyl acrylate, methyl methacrylate, and the DMAPMANCEPA monomer prepared in Example 3 in a weight ratio of 30:70:0.7 was conducted in the presence of approximately 25 weight percent, based on the total weight of monomer, of the polyurethane dispersant.

The resulting copolymer was evaluated in a semi-gloss paint formula at 25% pigment volume concentration (PVC). The paint was evaluated for scrub resistance according to ASTM D 2486 using scrub resistance equipment Model #D10V available from Paul N. Gardner Company, in Pampano Beach, Fla. USA. The paint exhibited significantly higher wet adhesion (470 cycles) than a control containing no DMAPMA/CEPA monomer (270 cycles).

EXAMPLE 13

A mortar composition was prepared which contained the copolymer prepared in Example 12. The mortar composition exhibited a creamy, smooth texture which indicated mortar compatibility. In addition, the mortar composition provided easier pumping and filling of forms.

Changes and modifications may be made by those of ordinary skill within the scope and spirit of the following claims.

What is claimed is:

1. A zwitterionic monomer having amino-multicarboxylic acid functionality having Structure (I)

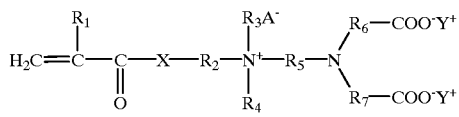

wherein $R_1$ is selected from the group consisting of H, an alkyl group having 1 to 6 carbon atoms; $R_2$ is $(CH_2)_n$ where n is 2 to 12; $R_3$ and $R_4$ are independently an alkyl group having 1 to 6 carbon atoms; $R_5$ is $(CH_2)_m$ where m is 2 or 3; $R_6$ and $R_7$ are independently selected from

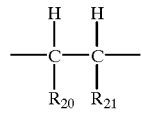

wherein $R_{20}$ is selected from the group consisting of H, $CH_3$, and COOY; $R_{21}$ is selected from H or $CH_3$; X is oxygen or nitrogen; A is a halide; and Y is independently a cation.

2. The zwitterionic monomer as claimed in claim 1 wherein Y is independently selected from the group consisting of H, alkali metal, alkaline earth metal, and ammonium.

3. A polymerization product of a zwitterionic monomer as claimed in claim 1.

4. A hair treating composition comprising a polymer prepared from the monomer as claimed in claim 1.

5. A coating composition comprising a polymer prepared from the monomer as claimed in claim 1.

6. A mortar composition comprising a polymer prepared from the monomer as claimed in claim 1.

* * * * *